United States Patent
Balcke et al.

(10) Patent No.: US 9,820,919 B2
(45) Date of Patent: *Nov. 21, 2017

(54) EMULSIFIER-FREE, SKIN-CONDITIONING COSMETIC OR DERMATOLOGICAL PREPARATION HAVING A GRANULAR STRUCTURE FOR USE ON WET SKIN

(71) Applicant: Beiersdorf AG, Hamburg (DE)

(72) Inventors: Isabel Balcke, Hamburg (DE); Sabine Schulz, Hamburg (DE); Guido Heinsohn, Glueckstadt (DE); Julia Eckert, Hamburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/784,387

(22) PCT Filed: Mar. 25, 2014

(86) PCT No.: PCT/EP2014/055954
§ 371 (c)(1),
(2) Date: Oct. 14, 2015

(87) PCT Pub. No.: WO2014/170100
PCT Pub. Date: Oct. 23, 2014

(65) Prior Publication Data
US 2016/0058676 A1 Mar. 3, 2016

(30) Foreign Application Priority Data
Apr. 15, 2013 (DE) .................. 10 2013 206 718

(51) Int. Cl.
*A61K 8/04* (2006.01)
*A61K 8/31* (2006.01)
*A61K 8/34* (2006.01)
*A61K 8/81* (2006.01)
*A61K 8/92* (2006.01)
*A61Q 19/00* (2006.01)
*A61K 8/02* (2006.01)

(52) U.S. Cl.
CPC .............. *A61K 8/04* (2013.01); *A61K 8/0241* (2013.01); *A61K 8/31* (2013.01); *A61K 8/342* (2013.01); *A61K 8/8147* (2013.01); *A61K 8/8152* (2013.01); *A61K 8/92* (2013.01); *A61Q 19/00* (2013.01); *A61K 2800/30* (2013.01); *A61K 2800/33* (2013.01); *A61K 2800/412* (2013.01); *A61K 2800/652* (2013.01); *A61K 2800/805* (2013.01); *A61Q 19/007* (2013.01)

(58) Field of Classification Search
CPC ............ A61K 2800/30; A61K 2800/33; A61K 2800/412; A61K 2800/652; A61K 2800/805; A61K 8/0241; A61K 8/04; A61K 8/31; A61K 8/342; A61K 8/8147; A61K 8/8152; A61K 8/92; A61Q 19/00; A61Q 19/007
See application file for complete search history.

(56) References Cited

U.S. PATENT DOCUMENTS

| | | | |
|---|---|---|---|
| 7,977,289 B2 | 7/2011 | Patel et al. | |
| 8,933,125 B2 | 1/2015 | Ishii et al. | |
| 9,259,378 B2 * | 2/2016 | Balcke | A61K 8/04 |
| 2005/0238605 A1 | 10/2005 | Kohlhase et al. | |
| 2009/0281013 A1 | 11/2009 | Patel | |
| 2011/0071223 A1 | 3/2011 | Ishii et al. | |
| 2013/0108572 A1 * | 5/2013 | Balcke | A61K 8/342 424/73 |
| 2014/0127147 A1 | 5/2014 | Klug et al. | |

FOREIGN PATENT DOCUMENTS

| | | | |
|---|---|---|---|
| DE | 10246160 A1 | 4/2004 | |
| DE | 102004003435 A1 | 8/2005 | |
| DE | 102011013342 A1 | 9/2011 | |
| DE | 202012000164 U1 * | 1/2012 | ............ A61K 8/342 |
| EP | 1090627 A1 | 4/2001 | |
| EP | 2174639 A1 | 4/2010 | |
| WO | 03075881 A1 | 9/2003 | |
| WO | 03094867 A1 | 11/2003 | |
| WO | 2013064391 A2 | 5/2013 | |

OTHER PUBLICATIONS

Pharmazeutische Technologie [Pharmaceutical technology] Kurt H. Bauer, Karl-Heinz Frömming, Claus FürhrerThieme Verlag, ISBN 3-13-692501-7, chapter 11, p. 312.

\* cited by examiner

*Primary Examiner* — Michael B. Pallay
(74) *Attorney, Agent, or Firm* — Abel Law Group, LLP (57) ABSTRACT

The invention comprises an emulsifier-free, skin-conditioning, cosmetic or dermatological preparation having a granular structure, characterized by contents of fatty alcohols and wax or paraffin for use on wet skin. The preparation is characterized by a special production method, which in turn only brings about the advantageous properties of a skin conditioning.

20 Claims, 5 Drawing Sheets

EMULSIFIER-FREE, SKIN-CONDITIONING COSMETIC OR DERMATOLOGICAL PREPARATION HAVING A GRANULAR STRUCTURE FOR USE ON WET SKIN

BACKGROUND OF THE INVENTION

1. Field of the Invention

The invention comprises an emulsifier-free, skin-conditioning cosmetic or dermatological preparation. The preparation is characterized by a specific production, which in turn only brings about the advantageous properties of a skin conditioning.

The preparation is suitable for application to wet skin without being completely rinsed off and therefore facilitates rubbing in cream while showering.

2. Discussion of Background Information

Rubbing in cream under wet conditions, skin care under the shower, is summarized as skin conditioning. This means inter alia:
1. Use of a customary shower product for cleaning the skin, rinsing off
2. Application/spreading of the preparation according to the invention to wet skin
3. Showering off again with warm or cold water
4. Drying the skin.

Cosmetic or dermatological preparations can be divided on the basis of their application time and their intended use. Some products are washed off immediately after use ("rinse-off"), while others are intended to remain for longer on the skin and have an effect there ("leave-on").

Cosmetic preparations for caring for the skin are developed primarily for use on dry skin. This preparation form is known as leave-on preparations, such as creams, lotions or body milk. These are often formulated as emulsions, in particular W/O, O/W, O/W/O or W/O/W emulsions.

Emulsions are generally understood as meaning heterogeneous systems which consist of two immiscible liquids or liquids that have only limited miscibility with one another, these usually being referred to as phases. In an emulsion, one of the two liquids (water or oil) is dispersed in the form of very fine droplets in the other liquid. The liquids (pure or as solutions) are present in an emulsion in a more or less fine distribution, which generally has only limited stability.

If the two liquids are water and oil, and oil droplets are present in fine distribution in water, then this is an oil-in-water emulsion (O/W emulsion, e.g. milk). The basic character, for example electrical conductivity, sensory properties, ability of the continuous phase to be colored, of an O/W emulsion is determined by the water. In a water-in-oil emulsion (W/O emulsion, e.g. butter), the principle is reversed, the basic character here being determined by the oil.

Leave-on preparations are unsuitable for use on wet or moist skin. On account of the emulsifiers contained, they can emulsify water and, on account of the lipids, sometimes leave behind an oily film.

By contrast, rinse-off preparations are designed for use under the shower or during bathing. By contrast, rinse-off preparations, however, involve to a lesser extent the care aspect as is obtained upon rubbing in cream.

It is desirable to provide a preparation which both takes into consideration the care aspect and can be applied as rinse-off, for example under the shower.

One property of cosmetic products that is very important to the consumer but can only be measured quantitatively with difficulty is their texture and sensory properties. The term "texture" is understood as meaning those properties of a cosmetic which are attributed to the constitution of the preparation, and can be perceived by sense of feel and touch and in some cases expressed in terms of mechanical or rheological flow properties. The texture can in particular be tested by means of sensorics. The texture of cosmetic products, which can optionally be influenced with the help of additives, is of virtually identical importance to the consumer as their effects which can be ascertained objectively.

The term "sensorics" refers to the scientific discipline which deals with the evaluation of cosmetic preparations on the basis of sensory impressions. The sensory assessment of a cosmetic is made on the basis of the visual, olfactory and haptic impressions.

visual impressions: all features that can be perceived by eye (color, shape, structure).

olfactory impressions: all odor impressions that can be perceived upon breathing in air through the nose, which can often be differentiated into initial odor (top note), main odor (medium note, body) and after-odor (finale). The volatile substances only released upon application also contribute to the olfactory impression.

haptic impressions: all sensations of the sense of touch which concern primarily constitution and consistency of the product.

The sensory analysis makes use of the possibility of ascertaining the overall sensory impression of a product integrally. Disadvantages of sensory analysis are the subjectivity of the impression, the ease with which the test subjects can be influenced and the considerable scattering of the results brought about as a consequence. These failings are nowadays countered by using groups of trained test subjects, mutual shielding of the testers, and statistical evaluation of the mostly extensive analytical data.

It was therefore a further object of the present invention to provide preparations which, besides the criteria customary for cosmetics such as compatibility, storage stability and the like, also offer the consumer essential, hitherto unknown cosmetic, in particular sensory, benefits. In particular, the sought preparations should be suitable for use in the body care sector, i.e. for use on the entire body, and at the same time be sensorily attractive.

SUMMARY OF THE INVENTION

The invention is a skin-conditioning, cosmetic or dermatological preparation obtainable by
- a.) mixing of one or more polyacrylic acid polymers in water with the input of energy,
- b.) melting of one or more fatty alcohols and
  - b1) at least one additional wax and/or
  - b2) a mixture of liquid and solid hydrocarbons,
  - where at least the hydrocarbon mixture has a melting range from 5° C. to 75° C., preferably up to 55° C. (according to DSC),
- c.) combining of the mixtures a.) and b.) with stirring, with complete homogenization being avoided, and
- d.) optional addition of one or more substances selected from the group of neutralizing agents, skin moisturizers, preservatives, oils, thickeners and perfumes.

Here, no emulsifiers are added to the preparation.

Preferably, in step b.), one or more fatty alcohols, at least one wax (b1) and a mixture of liquid and solid hydrocarbons (b2) are melted.

Preferably, the fatty alcohol or fatty alcohols and also the wax or the waxes also have a melting range from 5° to 75° C. according to DSC.

BRIEF DESCRIPTION OF THE DRAWINGS

In the accompanying drawings.

DETAILED DESCRIPTION OF THE INVENTION

The preparations according to the invention are otherwise obtainable as customary polyacrylic acid polymer-containing preparations.

Upon adding polyacrylic acid polymers to water, a swelling is expected, meaning that then higher energy is required in order to avoid ensuing clumping. This has led to the incorporation of the polyacrylic acid polymers in oils being carried out.

The known production practice therefore prescribes that the sometimes "dusty" polyacrylic acids should be predispersed in a lipid and only then be added to the water phase.

However, according to the invention and contrary to this statement, the polyacrylic acid polymers are now dispersed in water. Surprisingly, this leads to the polyacrylic acid polymers being more "activated" as a result of this production mode than if they are wetted with lipid.

This is evident inter alia from the fact that the preparation then obtainable in this way forms for the first time a perceptible residue on the skin which can also be detected by the user.

The required input of energy is primarily understood as meaning stirring, but also other dispersion known to the person skilled in the art is to be understood by this, such as, for example, with the help of Ultraturax (high input of energy).

The incorporation of the polyacrylic acid polymers into the water phase in step a.) takes place with the help of a higher input of energy with complete homogenization as far as possible.

By contrast, no complete homogenization is prescribed in step c.).

The combination with the introduction of heat can also be applied according to the invention.

When preparing fatty phase b.), the fatty alcohols are melted together with the waxes (b1) and/or mixtures of liquid and solid hydrocarbons (b2). It is in accordance with the invention to mix fatty alcohols and waxes, fatty alcohols and mixture of hydrocarbons and fatty alcohols with waxes and a mixture of hydrocarbons in phase b.).

The temperature here depends on the melting temperature of the individual constituents, and is preferably above 74° C.

Stirring is advantageously carried out during the melting operation so that localized areas of overheating do not arise.

Only then are the two phases a.) and b.) combined. During the processing in step c.) it has surprisingly been found that in the event of the introduction of too much energy, i.e. complete homogenization, during the combining and mixing of the two phases, a satisfactory product is not obtained. The product obtained is then too smooth, too fine and too amorphous.

An incomplete homogenization is essential to the invention. This means that optically anisotropic, i.e. crystalline areas, a so-called granular structure, can be established by means of investigations by polarizing microscope.

This granular structure, which differs from liquid crystalline structures, is described in more detail for example in the text book "Pharmazeutische Technologie [Pharmaceutical technology]" Kurt H. Bauer, Karl-Heinz Frömming, Claus FührerThieme Verlag, ISBN 3-13-692501-7, chapter 11, page 312 ff for hydrocarbon-containing preparations, vaselines.

In a comparative experiment, customary polyacrylic acid polymer preparations, emulsion-based, were compared with preparations according to the invention (example 2).

To prepare the sample, two microscope cover slips are placed on a microscope slide at a distance of ca. 1 cm. A small amount of the respective sample is placed between the cover slips and squeezed in order to obtain a precisely defined layer thickness of the preparation of ca. 0.15 mm.

The samples are then viewed via a transmitted-light microscope equipped with two linear polarization filters (e.g. stereo microscope Motic DM-143 FBGG, with 4× zoom and 3 megapixel camera).

Crossed linear polarization filters are used here in order to increase the optical contrast.

A suitable magnification (20×) is selected and an image is taken with the digital camera.

FIGS. 1, 2, 3 and 6 show the images obtained in this way.

Figure 1:
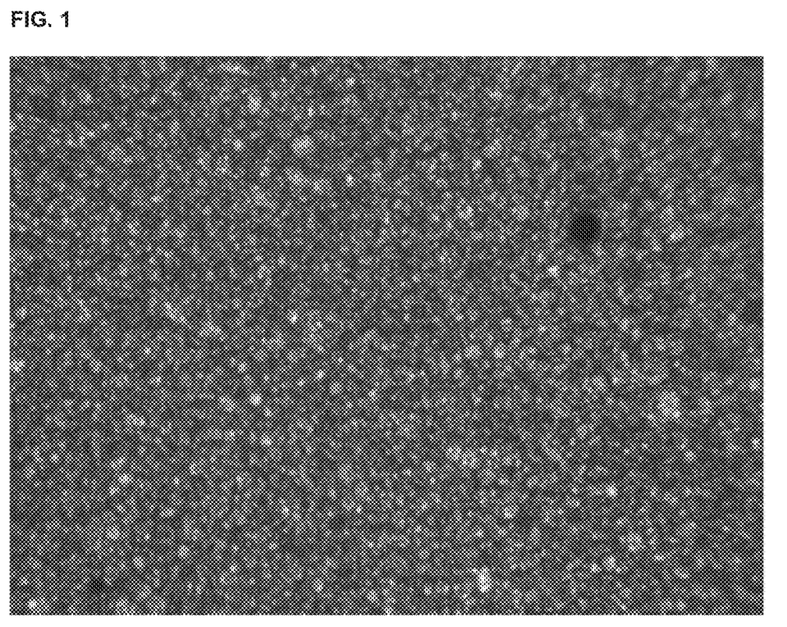
FIG. 1 shows a photograph of a layer of a preparation according to the present invention viewed under a transmitted-light microscope.
Figure 2:
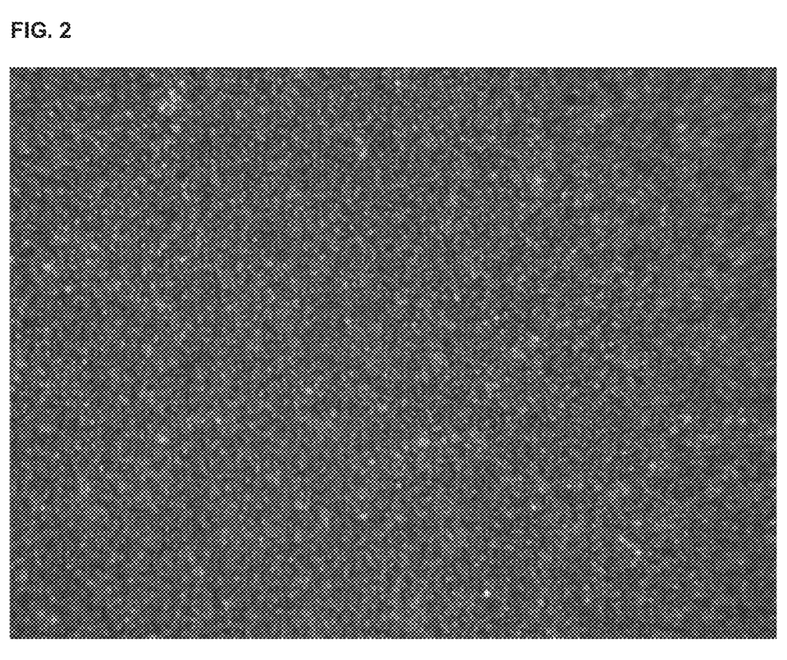
FIG. 2 shows a photograph of a layer of another preparation according to the present invention viewed under a transmitted-light microscope.
Figure 3:
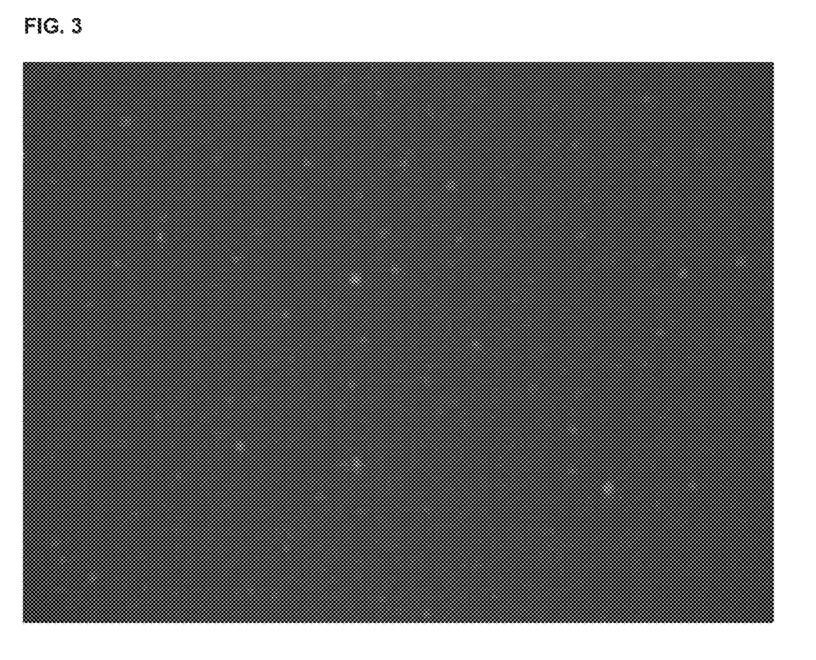
FIG. 3 shows a photograph of a preparation of the prior art viewed under a transmitted-light microscope.
Figure 6:
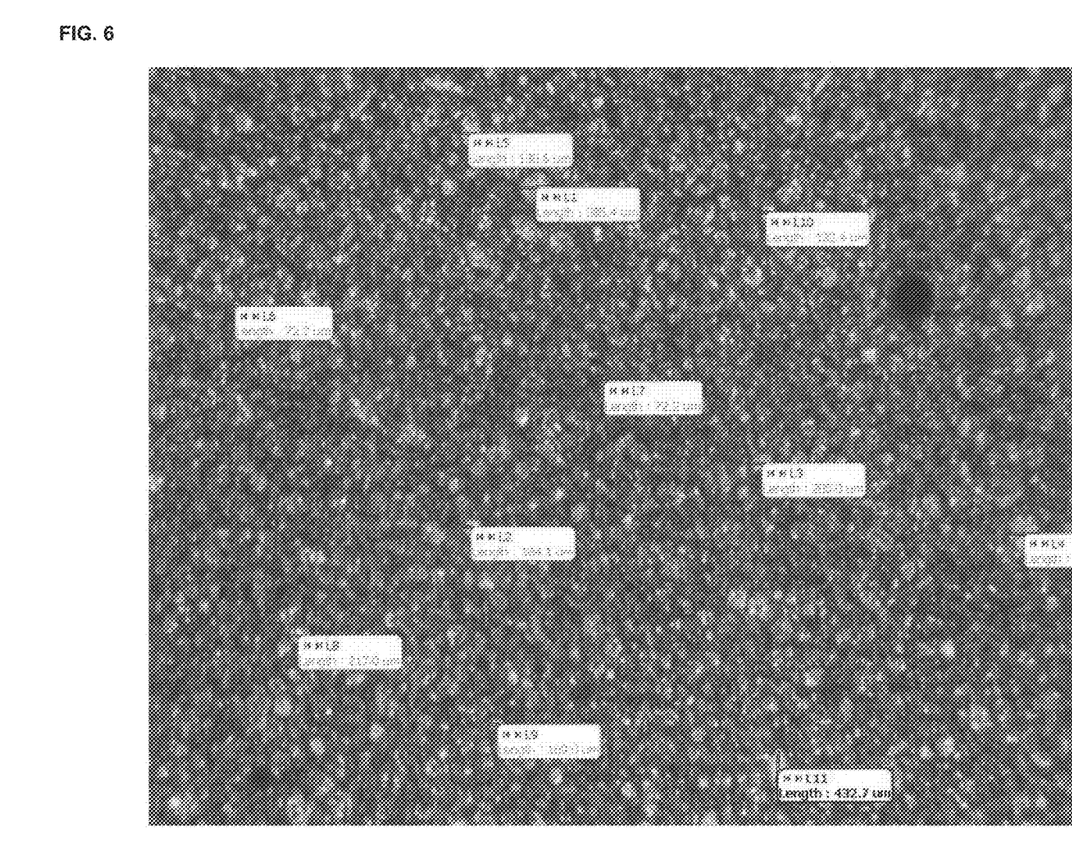
FIG. 6 shows a photograph of a layer of another preparation according to the present invention viewed under a transmitted-light microscope.

FIGS. 1, 2 and 6 show preparations according to the invention with a recognizable granular structure, so-called crystallites. The preparations according to the invention have a so-called grainy performance, and are referred to as grainy.

The known prior art preparation forms (FIG. 3) show a fine texture without recognizable granular structure or crystallites.

The grainy texture according to the invention is achieved if one or more crystallites with a particle size of 5 to 500 μm are present on 4 mm² area of the preparation in a layer thickness of 0.15 mm (+/−0.02 mm).

This data is accessible and reworkable for example via the presented light microscopic investigations and shown by way of example in FIG. 6.

The particle size is a measure of the diameter of the particles.

According to the invention, therefore, a complete homogeneous incorporation of the fatty phase into the aqueous phase is dispensed with so as not to obtain a smooth, fine product.

Only the so-called graininess constitutes the product performance of skin conditioning advantageous for the user.

It was found that only this product property, which is brought about by the production process, leads to the preparations according to the invention and no smooth preparations are obtained.

If a product is too smooth, the product slides off from the skin too rapidly, a film is unable to form and skin conditioning does not take place.

In this connection, smooth means inter alia also that an excessively thin product with a viscosity of less than 4000 mPas is obtained, which likewise does not bring about the desired product performance.

Preparations according to the invention are therefore preferably characterized by a viscosity of 4000 mPas and above (Rheomat 123 from proRheo, spindle 1 at T=25° C.) and/or a granular structure, characterized by one or more crystallites with a particle size of 5 to 500 μm on 4 mm² area of the preparation in a layer thickness of 0.15 mm (+/−0.02 mm; ascertained via a transmitted-light microscope equipped with two linear polarization filters and a 20× magnification).

The definition of the term "particle size" is to be understood as follows. Particles are three-dimensional structures which may be solid and/or liquid and have a structure that can be delimited from the surroundings.

The particles consist essentially of the fatty phase. They should be differentiated from the surroundings since these particles are stabilized by the gel network (surroundings). In this connection, some of the fatty phase can also be located in the gel network. What is decisive therefore is not a 100% separation between gel network (surroundings) and fatty phase, but the formation according to the invention of the granular structure with a particle density of one or more crystallites with a particle size of 5 to 500 μm on 4 mm² area of the preparation.

Three parameters (length, width, height) are required in order to be able to give a complete description of particle sizes. It is therefore actually difficult to describe a particle by stating a single number which corresponds to the particle size. In the majority of methods for determining size, it is therefore assumed that the material to be measured is spherical since a sphere is the only form which can be described using a single number (the diameter).

If the product comprises spherical particles, then the particle size is unambiguously defined by stating the sphere diameter, as according to the invention preferably in the range from 5 to 500 μm. However, the majority of the finely granular structures or crystallites does not consist of spheres, but of greater or lesser irregularly shaped particles which may in an extreme case be needle-like, and in another plate-like. The dispersity property of the individual particles can be described here by the particle volume and additional parameters such as sphericity (sphere similarity). Instead of the single-parameter function for spheres, a multi-parameter dispersity function is obtained, the determination of which is associated with considerable measuring expenditure. Such expenditure is only justified if it serves to obtain essential information about product properties.

Consequently, it is normal in practice and also according to the invention to limit oneself to stating a single-parameter distribution function for the particle size, the diameter for assumed spherical form of the particles.

The texture of the preparation according to the invention referred to as granular structure, particles, crystallites or graininess therefore essentially comprises fatty phase constituents which differ optically from the surroundings.

The care film which forms on the skin has been investigated in a further comparison, once after using a rinse-off product with integrated skin care aspects (Nivea cream soft shower gel) on its own (FIG. 4) and once after using the same product (Nivea cream soft shower gel) and subsequently using the preparation according to the invention (example 2, FIG. 5). After both uses, the skin is rinsed with water.

The measurements carried out in relation to refatting of the skin were made by IR-Imaging. The measurement technique is referred to as IR-ATR (InfraRed-Attenuated Total Reflectance).

It was found that only after using the preparation according to the invention does a care film visible by means of the mentioned measurement technique remain on the skin which can be detected. Detection takes place via the intensity of the hydrocarbon IR bands (CH-IR bands).

The care film according to the invention comprises a film which is formed on the skin and which comprises one or more lipids and/or skin moisturizers.

Figure 4:
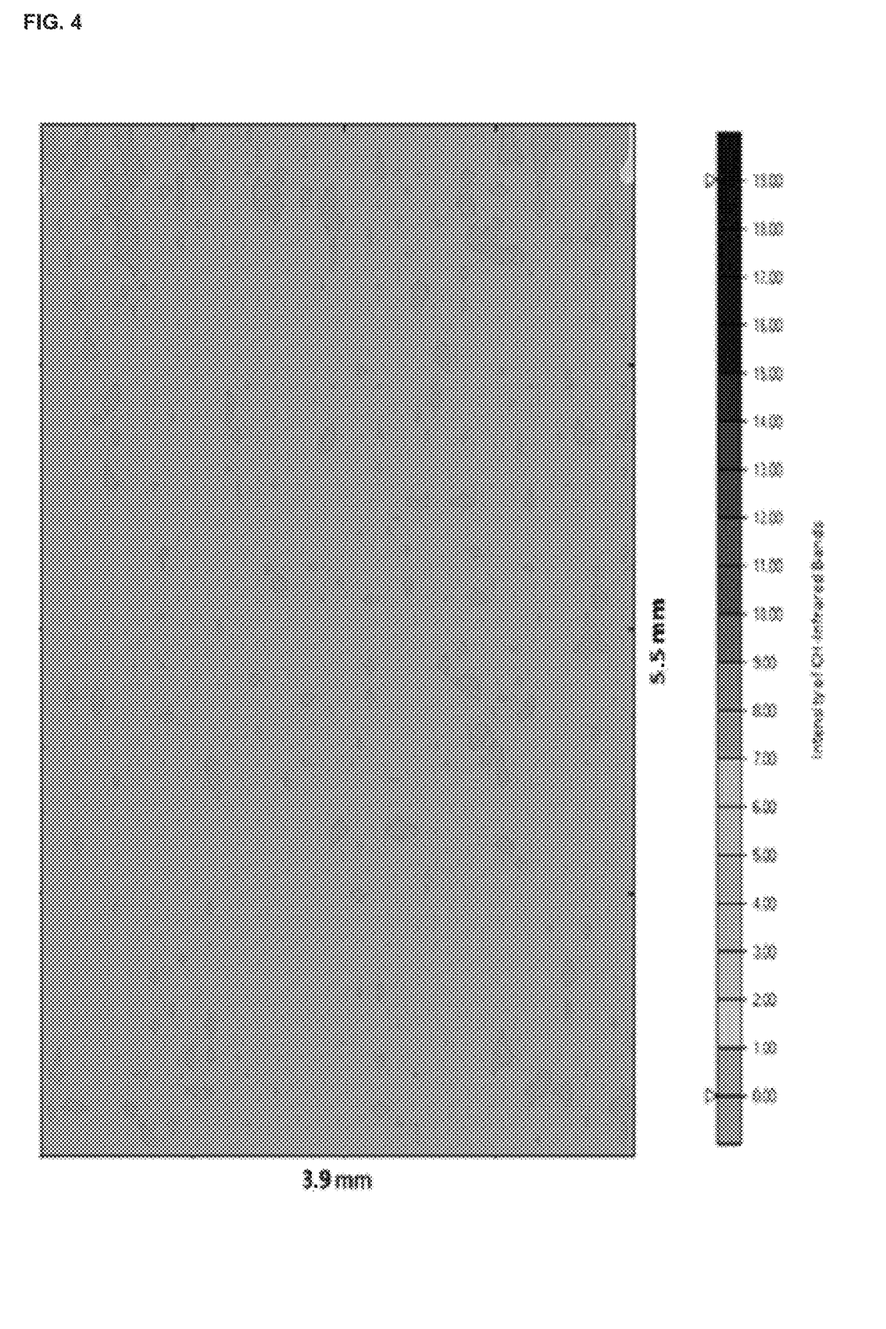
FIG. 4 is a representation of a layer of a preparation of the prior art based on data obtained by IR-ATR spectroscopy.
Figure 5:
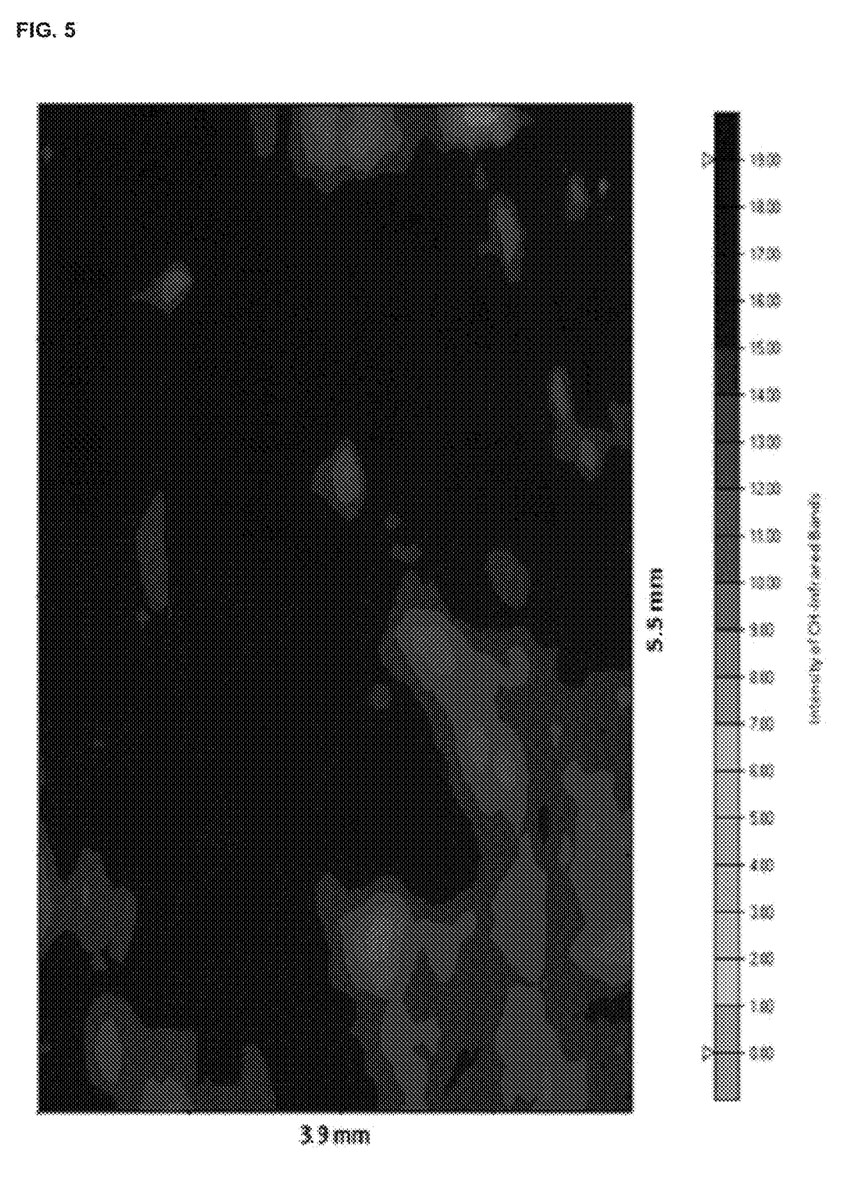
FIG. 5 is a representation of a layer of a preparation according to the present invention based on data obtained by IR-ATR spectroscopy.

FIGS. 4 and 5 show the comparison, the more gray the coloration, the more lipids there are on the skin. FIG. 5 shows a very significantly darker gray coloration than FIG. 4, which is proof of the care film according to the invention on the skin even after rinsing. The layer thickness of the film on the skin here is in the range up to 10 μm, which can be derived from the infrared spectra and the measurement technology.

The skin conditioning according to the invention comprises the rubbing in of cream under moist conditions, in particular skin care under the shower, where a care film remains on the skin even after rinsing. The care film can be detected by means of IR-ATR measurement technology and ideally has a thickness of at least 1 μm to 10 μm.

In particular, the skin conditioning according to the invention is notable for the fact that one or more lipids and/or skin moisturizers and no skin-barrier-harming substances, in particular no emulsifiers and/or surfactants, are present in the care film on the skin.

During the production of the preparation according to the invention, one or more fatty alcohols and at least one additional wax and/or mixture of liquid and solid hydrocarbons, with a melting range from 5° C. to 75° C., preferably up to 55° C. (according to DSC), are melted.

I.e. as well as at least one fatty alcohol, at least one wax is present or as well as fatty alcohol at least a mixture of liquid and solid hydrocarbons is present. Ideally, fatty alcohol, wax and a mixture of hydrocarbons are present.

Advantageous fatty alcohols selected are myristyl, cetearyl and/or stearyl alcohols, and the wax selected is Cera Microcristallina and the hydrocarbon mixture selected is paraffinum liquidum.

The fatty alcohols, waxes and hydrocarbon mixtures here all advantageously have a melting range from 5° C. to 75° C., preferably up to 55° C. (according to DSC).

DSC (Differential Scanning calorimetry) is a thermal method for measuring released/absorbed amount of heat of a sample during isothermal operation, heating or cooling (see DIN 53765, DIN 51007, ASTM E 474, ASTM D 3418). DSC is a comparative measurement method which permits the determination of amounts of heat of physical and chemical processes. If a material changes its physical state, such as e.g. melting or conversion of a crystal form to a different form or if it reacts chemically, heat is absorbed or released in the process. These amounts of heat can be measured quantitatively with the help of DSC. The method proceeds cyclically, meaning that after the first heating curve a defined cooling takes place and then the sample is heated once again in the stated temperature range. Two types of information are thus obtained: in the first heating curve, all thermal effects including past history are evident. In the second heating curve, the past history has been eliminated and the pure thermic behavior of the sample can be evaluated under defined cooling conditions. The melting range of the fatty alcohols, waxes and hydrocarbons between 4.5° C. and 75° C. according to DSC is the range ascertained in the first heating curve.

Waxes which can be used according to the invention are also fats and fat-like substances with wax-like consistency. These include inter alia fats (triglycerides), mono and diglycerides, natural and synthetic waxes, fatty and wax alcohols, esters of fatty alcohols and fatty acids, and also fatty acid amides or any desired mixtures of these substances.

The waxes are particularly preferably selected from the group of fats, in particular from the group of natural waxes:

Shorea stenoptera seed butter, hydrogenated vegetable oil, hydrogenated coco-glycerides, butyrospermum parkii butter, theobroma cacao (cocoa) seed butter, mango butter, hydrogenated palm kernel glycerides, hydrogenated palm glycerides, sunflower seed wax, soybean glycerides, butyrospermum parkii unsaponifiables, wool wax, cera alba, beeswax, sugar cane wax, cera carnauba, candelilla wax, Japan wax, hydrogenated rapeseed oil, shellac wax, hydrogenated lecithin, hydrogenated soybean oil, from the group of synthetic waxes, in particular from:

Cera Microcristallina, synthetic beeswax, synthetic wax, polyethylene, paraffin wax, ceresin, ozokerite from the group of fatty acids, in particular from:
palmitic acid, stearic acid,
from the group of fatty acid esters, in particular from:
cetearyl nonanoate, methyl palmitate, glyceryl tribehenate, glyceryl laurate, glyceryl stearate, cetyl palmitate; shea butter oleyl esters, PEG-8 beeswax.

The fatty alcohols used are preferably C14 to C22 fatty alcohols. Preferably, the fatty alcohols are selected from the group of linear fatty alcohols, in particular myristyl alcohol ($C_{14}H_{30}O$), cetyl alcohol (or palmityl alcohol) ($C_{16}H_{34}O$), stearyl alcohol (or octadecyl alcohol) ($C_{18}H_{38}O$) and cetylstearyl alcohol (cetearyl alcohol), behenyl alcohol, lanolin alcohol, a mixture of the alcohols cetyl alcohol (hexadecanol) and stearyl alcohol (octadecanol).

The fraction of C14-22 fatty alcohols in total is advantageously 3 to 14% by weight, in particular 7 to 9% by weight, based on the total mass of the preparation.

The weight ratio of the fatty alcohols C14, C18 and C16/18 is preferably selected as a:b:c in the range from a=0.5 to 2: B=1 to 3: c=2 to 6, in particular as 1:2:5.

The weight fractions are therefore to be selected advantageously in the range 0.5-1.5% by weight C14 fatty alcohols (C14), 1.5-2.5% by weight C18 fatty alcohols (C18) and 4-6% by weight C16/C18 fatty alcohols (C16/18), based on the total mass of the preparation.

The hydrocarbon mixtures used are preferably hydrocarbon gels or mixtures of liquid and solid paraffin hydrocarbons. Preferably, the content of solid hydrocarbons in the hydrocarbon mixture is between 1 and 50%, particularly preferably between 10 and 30%. The use of hydrocarbon mixtures which form fringed micelles and/or paracrystalline structures is advantageous.

The fraction of the hydrocarbon mixture in total is advantageously 1 to 50% by weight, in particular 20 to 30% by weight, based on the total mass of the preparation.

Fatty alcohol, in particular two or three fatty alcohols, is obligatorily present in the preparation according to the invention. In addition, one or more waxes is added to the preparation. Preferably, instead of the wax, a hydrocarbon mixture of hydrocarbons that are solid and liquid at room temperature can also be added.

Ideally, the preparation comprises all three constituents, fatty alcohols, waxes and hydrocarbon mixture.

Cosmetic or dermatological substances known to the person skilled in the art can then be added to the production and preparation according to the invention, in which case their addition must not adversely affect the skin-conditioning properties of the resulting preparation.

Thickeners, fillers and neutralizing agents are advantageously added to the preparations.

Thickeners are advantageously suitable for stabilizing the system and boost the skin-conditioning properties and the special skin feel of the preparations according to the invention.

The filler added is preferably aluminum starch octenylsuccinate, which likewise leads to an optimization of the skin feel by making the skin care film somewhat more velvety.

The neutralizing agent added is advantageously sodium hydroxide solution so that the thickeners can form their gel network and a stable system is produced.

The preparation according to the invention is emulsifier-free. I.e. the polyacrylic acid polymers which may have an emulsifying effect are not deemed to be emulsifiers according to the invention.

In other words, no further emulsifiers are added to the preparation besides the polyacrylic acid polymers.

Polyacrylic acid polymers are understood as meaning the polymers of acrylic acid and/or methacrylic acid and also acrylate crosspolymers known in cosmetics.

These are preferably polymers (macromolecules) with a high molecular weight (>1 mg/mol), which consist of a backbone of polyacrylic acid and small amounts of polyalkenyl ether crosslinkages. They are also referred to as carbomers.

These water-soluble or dispersible polymers can bring about a significant increase in viscosity in the liquid in which they are dissolved or dispersed. This is brought about by the formation of carbomer microgels in the water.

Besides the carbomers, particularly preferred polyacrylic acid polymers are those acrylate crosspolymers which exert a polymeric emulsifier effect.

Polymeric emulsifiers are primarily polyacrylic acid polymers with a high molecular weight. These emulsifying polyacrylic acid polymers have a small lipophilic fraction in addition to the main hydrophilic fraction. Within the context of the present invention, very particular preference is given to acrylate crosspolymers which have the INCI name "Acrylates/C10-30 Alkyl Acrylate Crosspolymer" and are available under the tradenames PemulenTR-1 and Pemulen TR-2 and also Carbopol 1342, Carbopol 1382 and Carbopol ETD 2020 from NOVEON.

The polyacrylic acid polymers are particularly preferably selected from the group of acrylates/C10-30 alkyl acrylate crosspolymers and/or carbomers. Particular preference is given to acrylates/C10-30 alkyl acrylate crosspolymer Pemulen® TR-1, e.g. from Lubrizol and Carbopol® 3128 from Lubrizol.

In this connection, a specific combination of polyacrylic acid polymers with an emulsifying effect, such as Pemulen TR-1 with other polyacrylic acid polymers, such as Carbopol 3128, which improve the sensory properties and ensure the stability of the preparation, especially at elevated temperatures, and a compound with free water is in accordance with the invention.

Particular preference is given here to a combination of three polyacrylic acid polymers, where one polyacrylic acid polymer has an emulsifying effect, such as e.g. Pemulen TR-1 or Pemulen TR-2, with other polyacrylic acid polymers which improve the sensory properties and ensure the stability of the preparation, especially at elevated temperatures (e.g. Carbopol 3128) and a polyacrylic acid polymer which improves the sensory properties upon absorbing free water (e.g. Carbopol 981).

Advantageously, therefore, preferably at least three polyacrylic acid polymers, in particular three polyacrylic acid polymers which differ in their properties, are added during the production of the preparation according to the invention.

The fraction of polyacrylic acid polymers in total is preferably 0.05 to 2% by weight, in particular 0.2 to 1% by weight, based on the total mass of the preparation.

The preparation according to the invention is obtained by the process steps according to the claims. Advantageously the combination of at least two polyacrylic acid polymers with at least two C14-22 fatty alcohols has proven to have improved stabilization of the preparation and in particular the skin feel during application to moist/wet skin is not unpleasant, not waxy, harsh or squeaky.

According to the invention, two polyacrylic acid polymers or three polyacrylic acid polymers are to be understood such that in each case one polyacrylic acid polymer differs from the others in each case in at least one property. The substance group acrylates/C10-30 alkyl acrylate crosspolymers includes for example the commercial products Pemulen TR-1 and TR-2.

Carbomers will differ for example in grades A, B and C. Differences are herein for example their gels with different viscosities (United States Pharmacopoeia, USP).

Moreover, a fraction of waxes or preferably a mixture of liquid and solid hydrocarbons with a melting range from 4.5 to 75° C., in particular up to 55° C. according to DSC is essential to the invention.

Oils which can be added to the preparations according to the invention are advantageously nonpolar to medium-polarity lipids. Otherwise, the stability is more difficult to establish on account of the freedom from emulsifier.

Within the context of the present disclosure, the expression "lipids" is used as a generic term for fats, oils, waxes and the like, as is entirely familiar to the person skilled in the art. The terms "oil phase" and "lipid phase" are also used synonymously.

Oils and fats differ inter alia in their polarity. It is proposed to adopt the interfacial tension towards water as a measure of the polarity index of an oil or of an oil phase. Here, the greater the polarity of the oil phase in question, the lower the interfacial tension between this oil phase and water. According to the invention, the interfacial tension is considered to be one possible measure of the polarity of a given oil component.

The interfacial tension is the force which acts upon an imaginary line of length one meter located at the interface between two phases. The physical unit for this interfacial tension is classically calculated according to the force/length relationship and is usually given in mN/m (milliNewtons divided by meters). It has a positive sign if it strives to reduce the size of the interface. In the converse case, it has a negative sign.

Preferred lipids are moreover medicinal white oils and silicone oils, particularly preferably naphthene-containing medicinal white oils, and also mixing products thereof.

The preparation according to the invention permits for the first time the application of care under the shower.

The preparations according to the invention are advantageously only formulated with preservatives which have a solubility in water of more than 0.75% at 20° C.

The absence of emulsifiers can otherwise lead to destabilizations and to crystallization.

The preparations according to the invention are furthermore preferably also free from surfactants.

Surfactants are substances which reduce the surface tension of a liquid or the interfacial tension between two phases and facilitate or support the formation of dispersions. Surfactants have the effect that two liquids that are in fact not miscible with one another, such as for example oil and water, can be dispersed.

Furthermore, surfactants are described as amphiphilic substances which are able to dissolve organic nonpolar substances in water. As a consequence of their specific molecular structure with at least one hydrophilic molecular moiety and one hydrophobic molecular moiety, they provide for a reduction in the surface tension of water, wetting of the skin, ease of soil removal and dissolution, ease of rinsing off and—if desired—foam regulation.

The hydrophilic moieties of a surfactant molecule are mostly polar functional groups, for example $-COO^-$, $-OSO_3^{2-}$, $-SO_3^-$, whereas the hydrophobic moieties are generally nonpolar hydrocarbon radicals. Surfactants are generally classified according to type and charge of the hydrophilic molecular moiety. In this connection, it is possible to differentiate between four groups:

anionic surfactants,
cationic surfactants,
amphoteric surfactants and
nonionic surfactants.

Anionic surfactants generally have carboxylate, sulfate or sulfonate groups as functional groups. In an aqueous solution, they form negatively charged organic ions in an acidic or neutral medium. Cationic surfactants are characterized almost exclusively by the presence of a quaternary ammonium group. In aqueous solution, they form positively charged organic ions in an acidic or neutral medium. Amphoteric surfactants contain both anionic and cationic groups and accordingly behave in aqueous solution like anionic or cationic surfactants depending on the pH. In a strongly acidic medium, they have a positive charge and in an alkaline medium they have a negative charge.

Furthermore, detersive substances, such as, for example, cationic surfactants, in particular quaternary ammonium compounds, are known. A detersive substance is used in laundry detergents, dishwashing detergents, shampoos and shower gels and refers to the fraction of the formulation which influences the washing or cleaning performance. Detersive substances increase the "solubility" of grease and dirt particles in water which adhere in the laundry or on the body. They may be of natural or synthetic origin. They are differentiated into anionic, cationic, ampholytic or nonionic depending on the nature of their charge.

Emulsifiers enable two immiscible liquids (for example oil in water) to be combined to give an emulsion. On account of the amphiphilic character, they penetrate into the oil with their fat-soluble moiety. As a result of the hydrophilic moiety, the oil droplet now formed by stirring can be "dispersed" in the aqueous environment. Emulsifiers primarily have no detersive, surface-active character.

Emulsifiers and surfactants can harm the barrier layer of the skin. Neither emulsifiers nor surfactants are therefore added to the preparations.

The preparations are used on wet skin and in particular also for shaving.

The preparation according to the invention can be used for conditioning the skin.

It permits the generation of a skin care film after application of the preparation to the skin and subsequent rinsing with water.

The care film that is formed is ideally at least 1 μm thick (measured according to IR-ATR measurement technology) and/or comprises no skin-barrier-harming substances, in particular no emulsifiers, surfactants, PEGs and/or organohalogen compounds.

The examples below illustrate the production according to the invention in order to obtain preparations according to the invention.

The numeric values are weight fractions, based on the total mass of the preparation.

EXAMPLES

| Water phase | 1 | 2 |
|---|---|---|
| Water | 50-60 | 53.8 |
| Acrylates/C10-30 Alkyl Acrylate Crosspolymer (Carbopol 3128) | 0.05-0.2 | 0.1 |
| Carbomer (Carbopol 981) | 0.01-0.1 | 0.02 |
| Acrylates/C10-30 Alkyl Acrylate Crosspolymer (Pemulen TR-1) | 0.05-0.2 | 0.1 |

| Fatty phase | 1 | 2 |
|---|---|---|
| Cera Microcristallina | 10-20 | 16.5 |
| Paraffinum Liquidum | 5-10 | 8.5 |
| Myristyl alcohol | 0.5-2 | 1.0 |
| Cetearyl alcohol | 2-10 | 5.0 |
| Stearyl alcohol | 1-4 | 2.0 |
| Hydrogenated cocoglycerides | 1-5 | 3.0 |
| Phenoxyethanol | 0.2-0.7 | 0.5 |

| Neutralizing phase | 1 | 2 |
|---|---|---|
| Sodium hydroxide solution 45% strength | 0.1-0.2 | 0.16 |
| Water | 1-3 | 2.0 |

| Perfume phase | 1 | 2 |
|---|---|---|
| Almond oil | 0.2-0.5 | 0.33 |
| Methylisothiazolinone | 0.05-0.1 | 0.09 |
| Perfume | 0.5-1 | 0.8 |

| Powder phase | 1 | 2 |
|---|---|---|
| Aluminum starch octenylsuccinate | 0.5-2 | 1.0 |
| Glycerol | 2-8 | 5.1 |

The constituents of the water phase are stirred at 25° C. for 4 min and then heated to 75° C. with stirring.

The constituents of the fatty phase are melted at 75° C. and stirred.

The water and fatty phases are combined with stirring at 75° C. with complete homogenization being avoided. This is achieved by establishing a grainy texture with one or more crystallites having a particle size of 5 to 500 μm per 4 mm² area of the preparation in a layer thickness of 0.15 mm (+1-0.02 mm).

The neutralizing, perfume and powder phases are then added with cooling to ca. 30° C. and finally the mixture is stirred.

What is claimed is:

1. An emulsifier-free cosmetic or dermatological preparation, wherein the preparation comprises one or more polyacrylic acid polymers, one or more fatty alcohols and (b1) at least one wax and/or (b2) a mixture of liquid and solid hydrocarbons, at least (b2) having a melting range according to DSC (Differential Scanning calorimetry) of from 5° C. to 75° C., and wherein the preparation has a granular structure comprising one or more crystallites having a particle size of from 5 to 500 μm on 4 mm² area of the preparation in a layer thickness of 0.15 mm+/−0.02 mm.

2. The preparation of claim 1, wherein at least (b2) has a melting range according to DSC of from 5° C. to 55° C.

3. The preparation of claim 1, wherein the preparation is free from skin-barrier harming substances.

4. The preparation of claim 1, wherein the preparation has a viscosity of at least 4000 mPas.

5. The preparation of claim 1, wherein the preparation comprises at least two polyacrylic acid polymers and at least two C14-22 fatty alcohols.

6. The preparation of claim 1, wherein the preparation comprises at least three polyacrylic acid polymers.

7. The preparation of claim 1, wherein the one or more polyacrylic acid polymers are selected from acrylates/C10-30 alkyl acrylate crosspolymers and/or carbomers.

8. The preparation of claim 1, wherein a total amount of the one or more polyacrylic acid polymers in the preparation is from 0.05% to 2% by weight, based on a total mass of the preparation.

9. The preparation of claim 8, wherein the total amount of the one or more polyacrylic acid polymers in the preparation is from 0.2% to 1% by weight.

10. The preparation of claim 1, wherein the preparation comprises at least three C14-22 fatty alcohols.

11. The preparation of claim 1, wherein a total amount of the one or more C14-22 fatty alcohols in the preparation is from 3% to 14% by weight, based on a total mass of the preparation.

12. The preparation of claim 11, wherein the total amount of the one or more C14-22 fatty alcohols in the preparation is from 7% to 9% by weight.

13. The preparation of claim 1, wherein the one or more fatty alcohols are selected from myristyl alcohol, stearyl alcohol, or cetearyl alcohol.

14. The preparation of claim 1, wherein the preparation is free from surfactants.

15. The preparation of claim 1, wherein the preparation has been obtained by a method which comprises
 (a) mixing one or more polyacrylic acid polymers in water with input of energy,
 (b) melting one or more fatty alcohols and
  (b1) at least one additional wax and/or
  (b2) a mixture of liquid and solid hydrocarbons,
  where at least (b2) has a melting range according to DSC (Differential Scanning calorimetry) of from 5° C. to 75° C.,
 (c) combining the mixtures obtained in (a) and (b) with stirring, but without complete homogenization being achieved, and (d) optional addition of one or more substances selected from neutralizing agents, skin moisturizers, preservatives, oils, thickeners, or perfumes.

16. The preparation of claim 15, wherein in (a) at least two polyacrylic acid polymers are mixed in water and in (b) at least two C14-22 fatty alcohols are melted.

17. The preparation of claim 15, wherein the one or more polyacrylic acid polymers mixed in (a) are selected from acrylates/C10-30 alkyl acrylate crosspolymers and/or carbomers.

18. A method of producing a skin care film of the preparation of claim 1 after application of the preparation to the skin and subsequent rinsing with water, wherein the method comprises applying the preparation in an amount to obtain a film having a thickness of least 1 µm according to IR-ATR.

19. A method of conditioning skin, wherein the method comprises applying to skin to be conditioned the preparation of claim 1.

20. A method of producing the cosmetic or dermatological preparation of claim 1, wherein the method comprises
- (a) mixing one or more polyacrylic acid polymers in water with input of energy,
- (b) melting one or more fatty alcohols and
  - (b1) at least one additional wax and/or
  - (b2) a mixture of liquid and solid hydrocarbons,
  - where at least (b2) has a melting range according to DSC (Differential Scanning calorimetry) of from 5° C. to 75° C.,
- (c) combining of the mixtures obtained in (a) and (b) with stirring but without complete homogenization being achieved, and
- (d) optional addition of one or more substances selected from neutralizing agents, skin moisturizers, preservatives, oils, thickeners, or perfumes.

\* \* \* \* \*